(12) United States Patent
Kurozumi et al.

(10) Patent No.: US 7,869,037 B2  
(45) Date of Patent: Jan. 11, 2011

(54) PARTICLE SIZE DISTRIBUTION MEASURING DEVICE

(75) Inventors: Takuji Kurozumi, Kyoto (JP); Yoshiaki Togawa, Kyoto (JP)

(73) Assignee: Horiba, Ltd. (JP)

( * ) Notice: Subject to any disclaimer, the term of this patent is extended or adjusted under 35 U.S.C. 154(b) by 251 days.

(21) Appl. No.: 12/174,983

(22) Filed: Jul. 17, 2008

(65) Prior Publication Data  
US 2009/0073438 A1    Mar. 19, 2009

(30) Foreign Application Priority Data  
Jul. 17, 2007    (JP)    ............... 2007-185943

(51) Int. Cl.  
*G01N 15/02*    (2006.01)

(52) U.S. Cl. ..................................... 356/336

(58) Field of Classification Search .............. None  
See application file for complete search history.

(56) References Cited

U.S. PATENT DOCUMENTS 7,180,592 B2 *    2/2007    Yoshioka et al. ............ 356/336

2007/0138438 A1 *    6/2007    Hampden-Smith et al. ....... 252/301.36

FOREIGN PATENT DOCUMENTS

| JP | 5-83138 | 4/1993 |
| JP | 2000-146814 | 5/2000 |

* cited by examiner

*Primary Examiner*—Tu T Nguyen  
(74) *Attorney, Agent, or Firm*—Cantor Colburn LLP

(57) ABSTRACT

This invention may measure the sprayed particle sprayed from the nozzle safely with the use of a conventional particle size distribution measuring device The particle size distribution measuring device may measure particle size distribution of a particle group, and may include a device body comprising a light source that irradiates light on the particle group and a light detector that detects intensity of diffracted light or/and scattered light generated by irradiation of the light, a spray measuring system that introduces a sprayed particle group as being the particle group sprayed from a nozzle into a measuring area between the light source and the light detector, and an ordinary measuring system that arranges a measuring cell that accommodates an ordinary particle group as being a particle group other than the sprayed particle group between the light source and the light detector are arranged to be exchangeable for each other.

7 Claims, 8 Drawing Sheets

PARTICLE SIZE DISTRIBUTION MEASURING DEVICE

CROSS-REFERENCE TO RELATED APPLICATION

This application claims priority under 35 USC 119 to Japanese application P2007-185943 filed Jul. 17, 2007.

BACKGROUND OF THE INVENTION AND RELATED ART STATEMENT

The present claimed invention relates to a particle size distribution measuring device, more specifically, an application for the particle size distribution measuring device that measures particle distribution based on intensity of diffracted light or/and scattered light generated by irradiation of the light on a particle group.

This kind of particle size distribution measuring device as shown in the patent document 1 irradiates the light from a light source such as a laser on a particle group accommodated in a transparent cell, detects angle distribution of intensity of diffracted light or/and scattered light generated at a time of light irradiation by multiple light detectors separately arranged around the cell, and measures the particle size distribution of the particle group based on the detected result.

However, the particle size distribution measuring device of the above structure is used to measure the particle group accommodated in the cell, and can not measure the particle size distribution of the particle group sprayed from a nozzle of a spray.

Thus. there is a problem that a dedicated measuring device as shown in, for example, the patent document 2 is required in order to measure the particle group sprayed from the nozzle of the sprayer.

[Patent document 1] Japan patent laid open number 2000-146814

[Patent document 2] Japan patent publication number 05-083138

SUMMARY OF THE INVENTION

The present claimed invention may solve all of the above-mentioned problems at once, and it may measure the sprayed particle sprayed from the nozzle by the use of a particle size distribution measuring device.

More specifically, the particle size distribution measuring device in accordance with at least an embodiment of this invention is to measure particle size distribution of a particle group, and may comprise a device body comprising a light source that irradiates light on the particle group and a light detector that detects intensity of diffracted light or/and scattered light generated by irradiation of the light, a spray measuring system that introduces a sprayed particle group as being the particle group sprayed from a nozzle into a measuring area between the light source and the light detector, and an ordinary measuring system that arranges a measuring cell that accommodates an ordinary particle group as being a particle group other than the sprayed particle group between the light source and the light detector are arranged to be exchangeable for each other.

In accordance with this arrangement, it is possible both to measure the sprayed particle group sprayed from the nozzle and to measure a conventional ordinary particle group other than the sprayed particle group with a single particle size distribution measuring device. As a result, it is possible to enrich applications of the particle size distribution measuring device.

The spray measuring system may comprise a casing that is mounted on the device body and inside of which a measuring area to measure the sprayed particle group is provided, an introducing port that is arranged on the casing and that introduces the sprayed particle group into inside of the casing, and an optical window that is arranged on the casing and between the measuring area and the light source and between the measuring area and the light detector, wherein the spray measuring system is mounted on the device body by mounting the casing on the device body in a state that the ordinary measuring system is dismounted from the device body is represented as a concrete embodiment of the spray measuring system and a concrete embodiment to make it possible to change the spray measuring system.

With this arrangement, since the spray measuring system can be mounted on the device body just by mounting the casing on the device body, it is possible to mount the spray measuring system on the device body with ease. In addition, since the measuring area is covered by the casing, it is possible to measure the sprayed particle group stably without receiving an effect of disturbance such as the wind or the light from the outside and without contaminating the device body. Furthermore, it is possible to conduct a measurement safely even though the sprayed particle group is a measuring sample that is harmful to human body or environment such as solvent, pesticide or insecticide.

In order to preferably prevent a problem that a satisfactory measurement result can not be obtained because the sprayed particle group sprayed from the nozzle diffuses more than necessary until it reaches the measuring area, it is preferable that an introducing pipe that is arranged continuously to the introducing port and that opens toward the measuring area is further comprised. In this case, it is preferable that a length of the introducing pipe is variable.

In order to preferably deal with various kinds of sprayed particle groups or various kinds of objects to be measured, it is preferable that a distance between the measuring area and the introducing port is arranged to be variable.

Especially, it is represented that the casing comprises a casing body that has the optical window and that covers the measuring area and a front panel that has the introducing port, and a distance change tube body that is arranged between the front panel and the casing body and that changes the distance between the measuring area and the introducing port is further comprised.

It is preferable that a discharging port that is arranged in the casing and that discharges the sprayed particle group to the outside and a vacuum mechanism that vacuums up the sprayed particle group from the discharging port are further comprised. With this arrangement, since contamination in the casing and accumulation of the sprayed particle group in the casing can be prevented, it is possible to conduct a measurement stably.

In order to further prevent the contamination in the casing and to facilitate cleaning or maintenance of the spray measuring system, it is preferable that a tray that is arranged on an under surface of the casing and that accommodates liquid generated at a time when the sprayed particle group is liquefied is further included.

In order to prevent contamination of the device body and to further facilitate cleaning or maintenance of the spray measuring system, it is preferable that a disposable optical film is arranged on the optical window.

Thus, it is possible to measure the sprayed particle sprayed from the nozzle by the use of the particle size distribution measuring device.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which.

DETAILED DESCRIPTION OF THE PREFERRED EMBODIMENTS

One embodiment of the present claimed invention will be explained with reference to drawings.

Figure 1:
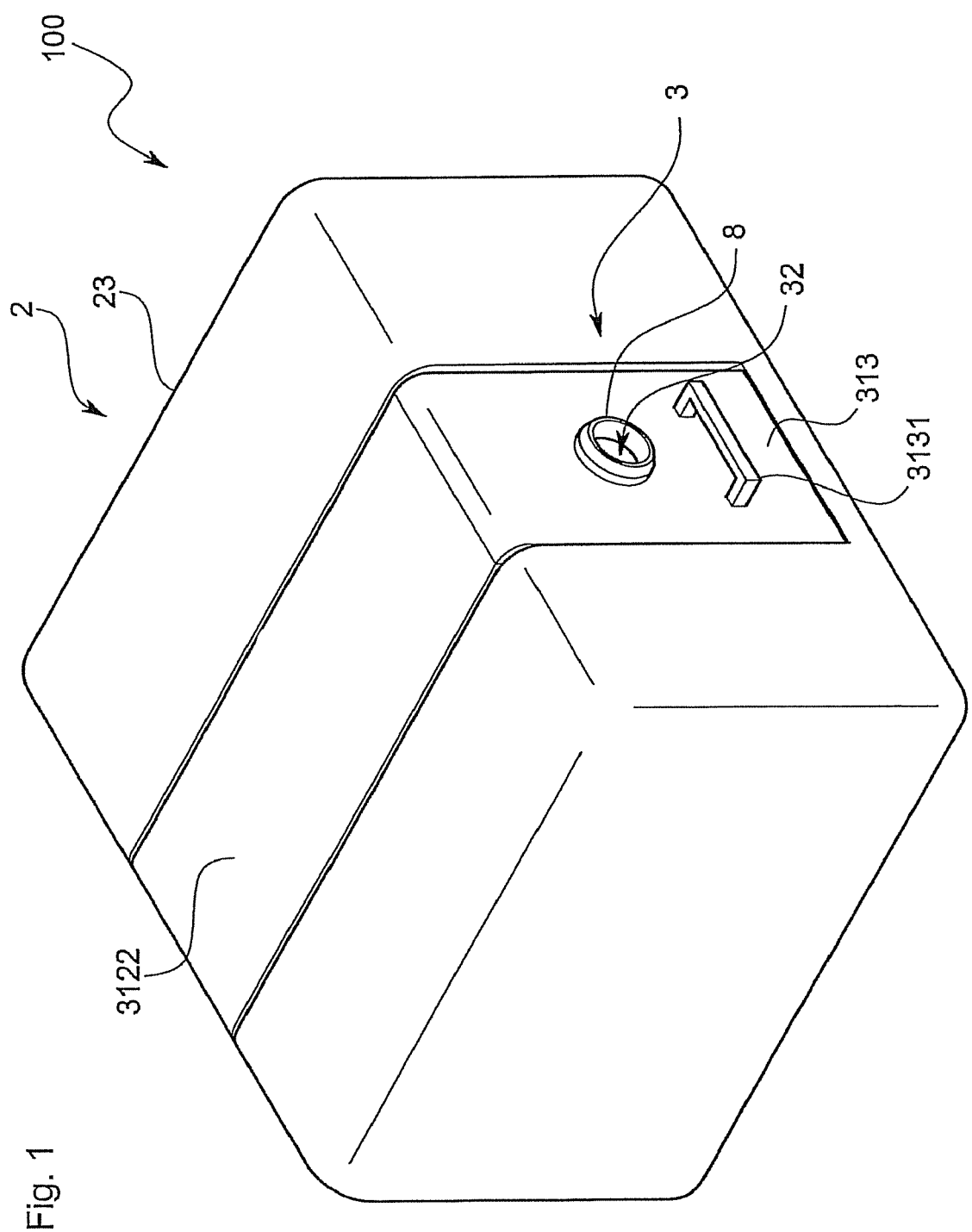
FIG. 1 is a perspective view of a particle size measuring device in accordance with this embodiment.
Figure 2:
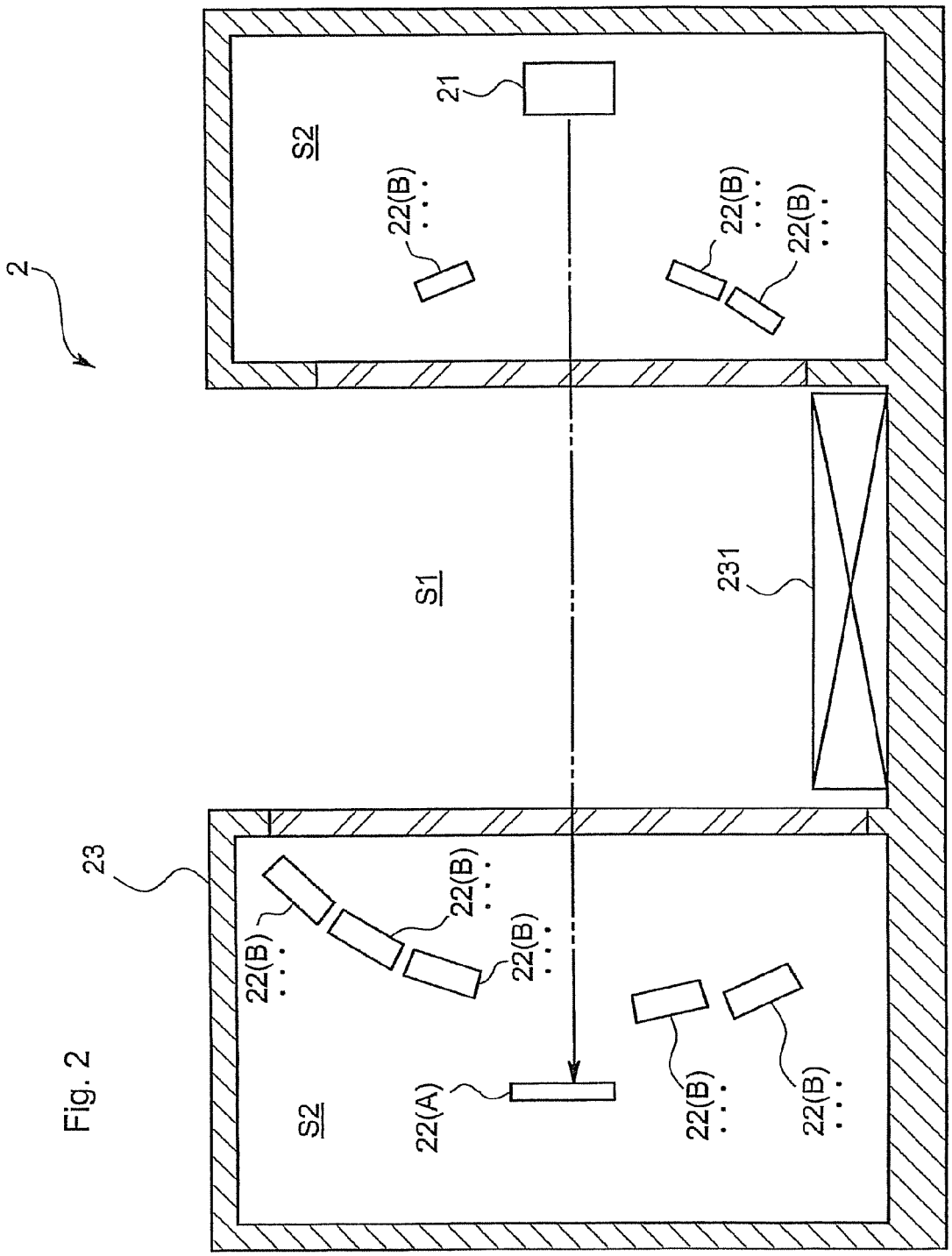
FIG. 2 is a pattern cross-sectional view of the particle size measuring device in accordance with this embodiment.
Figure 3:
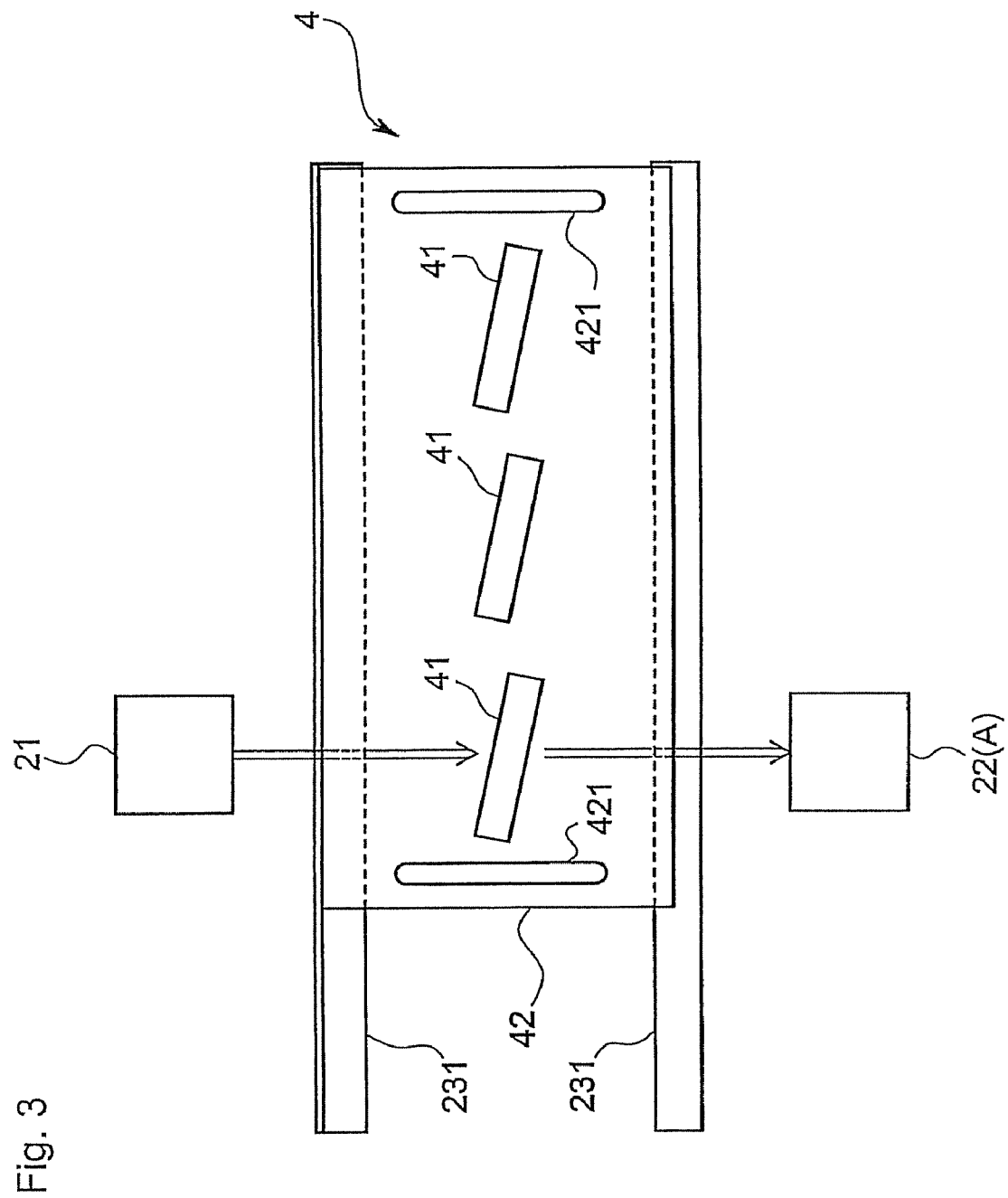
FIG. 3 is a pattern front view of an ordinary measuring system in accordance with this embodiment.
Figure 4:
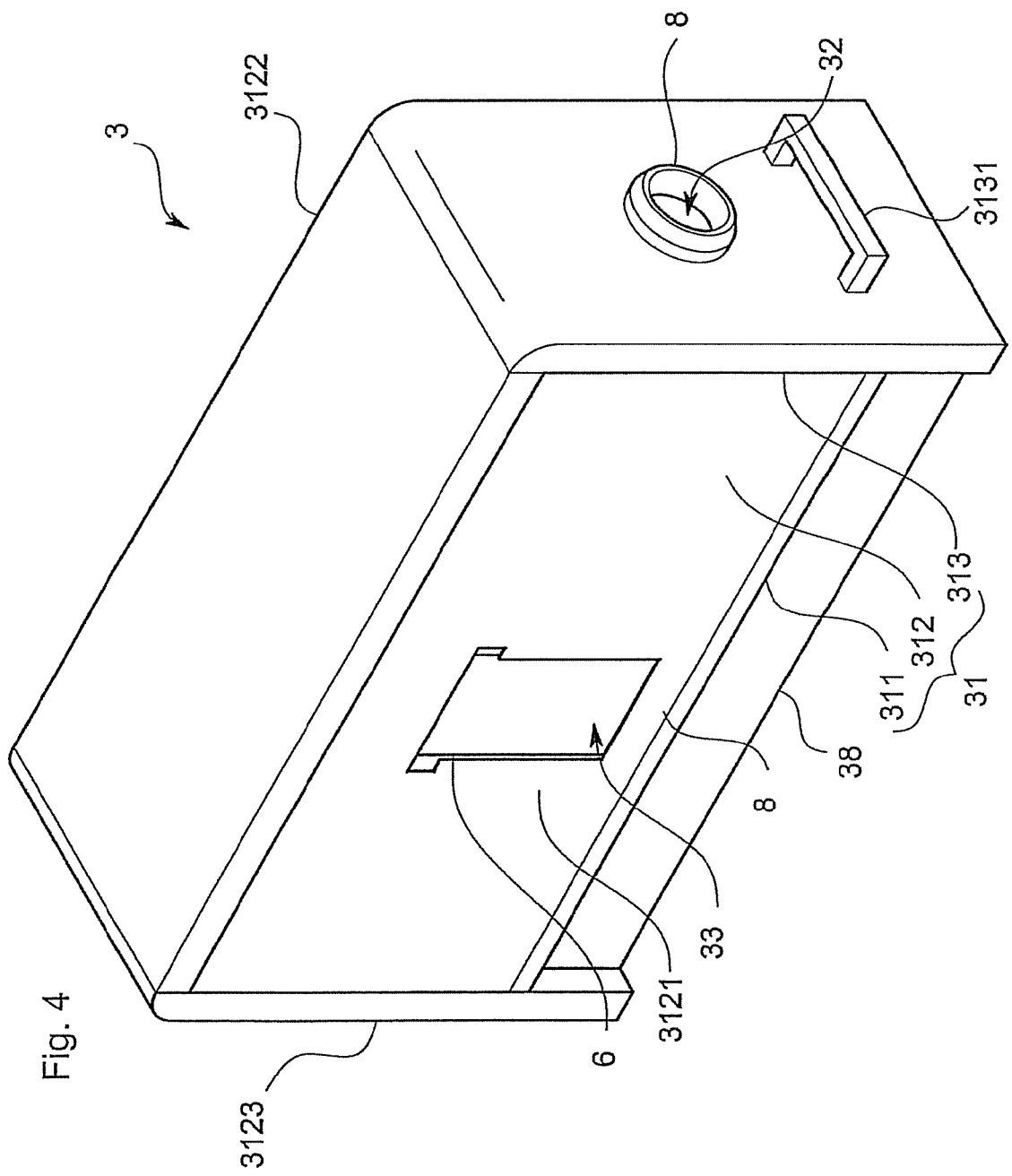
FIG. 4 is a perspective view of a spray measuring system in accordance with this embodiment.
Figure 5:
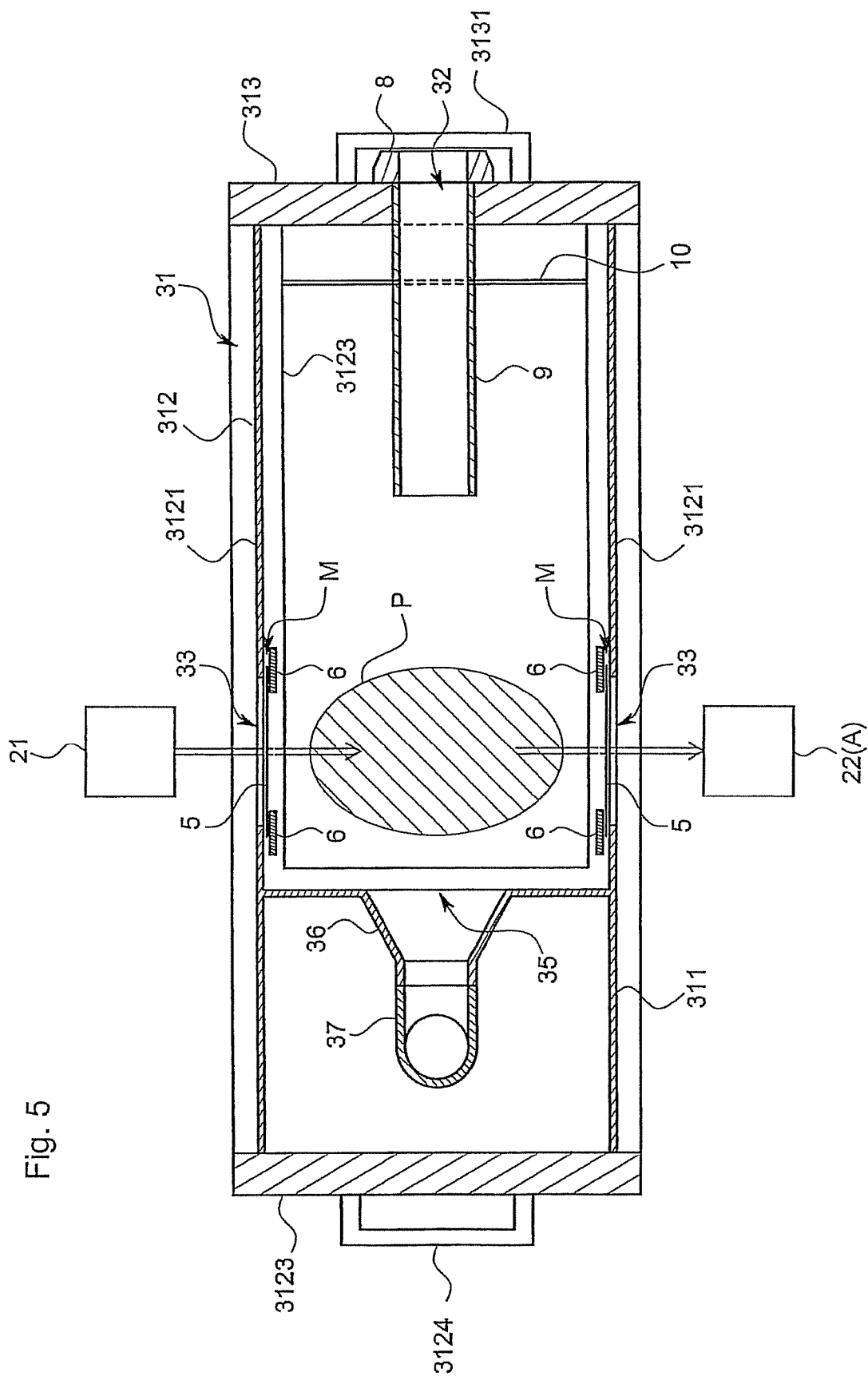
FIG. 5 is a cross-sectional view of the spray measuring system in accordance with this embodiment.
Figure 6:
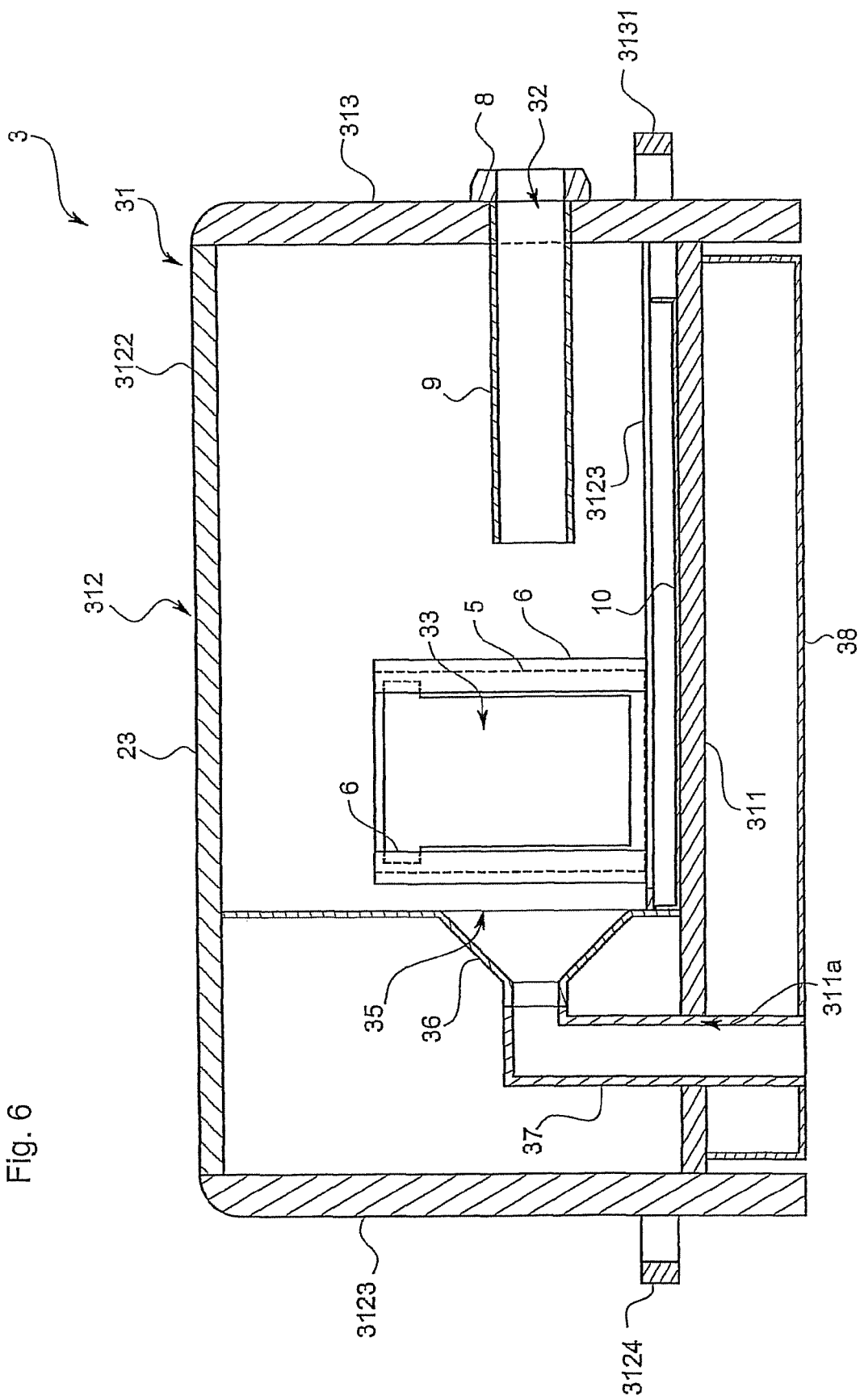
FIG. 6 is a longitudinal sectional view of the spray measuring system in accordance with this embodiment.
Figure 7:
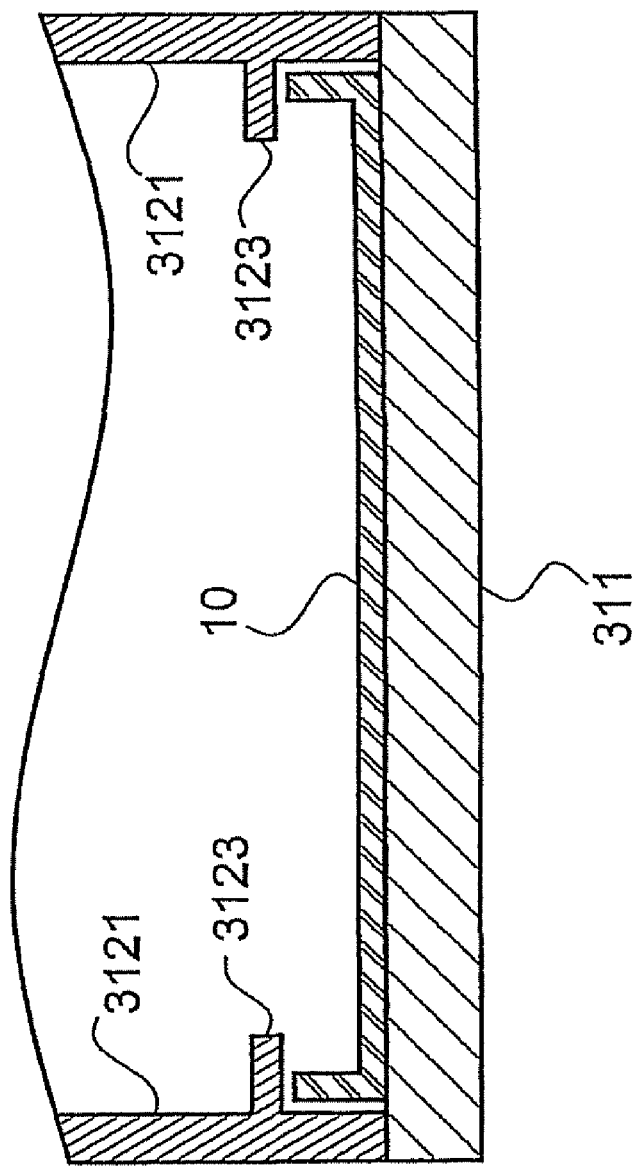
FIG. 7 is a partially enlarged cross-sectional view of the spray measuring system in accordance with this embodiment.

FIG. 1 is a pattern perspective view of a particle size distribution measuring device 1. FIG. 2 is a pattern cross-sectional view of a device body 2. FIG. 3 is a plane view mainly showing an ordinary measuring system. FIG. 4 is a perspective view of a spray measuring system 3. FIG. 5 is a pattern cross-sectional view of the spray measuring system 3. FIG. 6 is a longitudinal sectional view of the particle size distribution measuring device 1 mainly showing the spray measuring system 3. In addition, FIG. 7 is a partially enlarged cross-sectional view of the spray measuring system 3.

<Device Configuration>

The particle size measuring device 1 in accordance with this embodiment detects a diffracted and/or scattered pattern (an angle distribution of diffracted and/or scattered light intensity) of diffracted and/or scattered light generated at a time when light is irradiated on a particle group as being an object to be measured, conducts the reverse Fourier transformation on the diffracted and/or scattered pattern based on the MIE scattering theory, and measures particle size distribution. The particle size measuring device 1 comprises, in a large way, a device body 2, the spray measuring system 3 to measure a sprayed particle group as being a particle group sprayed from a nozzle of a spray, and an ordinary measuring system 4 to measure an ordinary particle group as being a particle group other than the sprayed particle group.

<Device Body 2>

The device body 2 comprises, as shown in FIG. 1 and FIG. 2, a light source 21 that irradiates light on the particle group, a light detector 22 that detects intensity of diffracted and/or scattered light generated by irradiation of the light and a housing 23 inside of which the light source 21 and the light detector 22 are accommodated.

The light source 21 is, for example, a semiconductor laser, and irradiates red laser light having a wavelength of, for example, about 650 nm. An optical axis of the laser light is set horizontally. An LED that irradiates blue light having a wavelength of, for example, about 400 nm may be used as the light source 21. Since the light having a longer wavelength is more advantageous to a case of measuring a particle having a big particle size and the light having a shorter wavelength is more advantageous to a case of measuring a particle having a small particle size, it is possible to broaden a measurable range of the particle size without degrading an accuracy of measurement if multiple light sources 21 that emit the light of various different wavelengths are arranged.

The light detector 22 makes use of a photodiode and outputs an electric signal (light intensity signal) having an intensity corresponding to a luminous intensity of the received light. A total number of the light detectors 22 is, for example, 90 through 100, and the light detectors 22 are arranged separately both around a cell 41 of the ordinary measuring system 4 or a measuring area P of the spray measuring system 3 and on a vertical plane including the cell 41 or the measuring area P.

Especially in this embodiment, as shown in FIG. 2, the light detectors 22 are classified into a narrow angle scattered light detector 22(A) for detecting the light that diffracts and/or scatters at an angle equal to or smaller than a certain angle with high accuracy and a wide angle scattered light detector 22(B) for detecting the light that diffracts and/or scatters from the front to the side or to the back at an angle wider than the certain angle. Multiple narrow angle scattered light detectors 22(A) are densely arranged concentrically on a board with a very narrow distance so as to be a ring detector array, and the wide angle scattered light detectors 22(B) are arranged several at a time in a blocked state or separately one by one.

The housing 23 has, as shown in FIG. 2, a measuring system accommodating space S1 that internally accommodates the spray measuring system 3, to be described later, or the ordinary measuring system 4, to be described later, and forms device accommodating spaces S2 that accommodate the light source 21 and the light detector 22 in a state to interpose the measuring system accommodating space S1 between the device accommodating space S2 and the device accommodating space S2.

In addition, at the bottom of the measuring system accommodating space S1, the housing 23 is provided with a rail member 31 on which the spray measuring system 3 and the ordinary measuring system 4 are placed.

The particle size distribution measuring device 1 of this embodiment is so arranged to make the ordinary measuring system 4 and the spray measuring system 3 exchangeable for each other to the device body 2 by making use of the rail member 231.

<Ordinary Measuring System 4>

The ordinary measuring system 4 places the measuring cell 41 that accommodates the ordinary particle group between the light source 21 and the light detector 22. The ordinary particle group is a particle group other than the sprayed particle group, and is dispersed in a dispersion medium and then accommodated inside the measuring cell 41.

More concretely, the ordinary measuring system 4 has, as shown in FIG. 3, a single or multiple cells 41 and a cell holding member 42 to hold the cell 41, and the cell holding member 42 is placed on the rail member 231 arranged in the measuring system accommodating space S1 so as to selectively locate the multiple cells 41 on positions on which the light from the light source 21 is irradiated.

Each of the multiple cells 41 is of different types (for example, a wet flow cell, a wet batch cell).

The cell holding member 42 is to move and slide the cell 41 on the rail member 231 arranged on the device body 2. The multiple cells 41 are selectively located at positions on which the light from the light source 21 is irradiated by the use of a handle 421 arranged at an end portion of the cell holding member 42.

<Spray Measuring System 3>

The spray measuring system 3 is of an integrated body that is mounted on the device body 2 from which the ordinary measuring system 4 is dismounted and that introduces the sprayed particle group as being the particle group sprayed from the nozzle into a position between the light source 21 and the light detector 22.

More concretely, the spray measuring system 3 comprises, as shown in FIG. 4 through FIG. 6, the casing 31 that is mounted on the device body 2 and inside of which the measuring area P to measure the sprayed particle group is provided, the introducing port 32 that introduces the sprayed particle group into the inside of the casing 31, and the optical window 33 arranged in the casing 31 between the measuring area P and the light source 21, and between the measuring area P and the light detector 22.

The casing 31 specifies an area (a sprayed area) to which the sprayed particle group is sprayed.

More concretely, the casing 31 is in a shape of a hollow cuboid comprising a board 311, a casing body 312 that is arranged on the board 311 and inside of which the measuring area P is provided and a front panel 313 detachably fixed to the casing body 312.

The board 311 has the same shape as that of the cell holding member 42 of the ordinary measuring system 4 and is placed on the rail member 231 of the housing 23.

The casing body 312 is arranged on the board 311 and forms the measuring area P. An upper wall 3122 of the casing body 312 functions as prevention of light-transmittance with closely attaching to an upper face of the device body 2 in a state that the spray measuring system 3 is mounted on the device body 2 in order to prevent incidence of the light from outside. In addition, the optical window 33 is arranged on each of right and left side walls 3121 of the casing body 312 respectively.

Each of the optical windows 33 is arranged between the measuring area P and the light source 21 and between the measuring area P and the light detector 22. The optical window 33 is generally in a shape of a vertically long rectangular viewed from a side and opens to a height including an angle so that the measuring area P can look on the light detector 22.

In addition, an optical film 5 made of disposable resin having optical transparency is mounted on the optical window 33. The optical film 5 mounted on the optical window 33 is fixed by means of a fixing means such as a clip or the like.

In this embodiment, a mounting mechanism M to mount the optical film 5 on the optical window 33 is arranged. The mounting mechanism M comprises a groove formed between the side wall 3121 and a guide plate 6 that is arranged near the side wall 3121 forming the optical window 33 and that faces the side wall 3121. The optical film 5 is mounted on the optical window 33 by inserting the optical film 5 into the groove. In this embodiment, a cut-out having a channel shape extending laterally is formed on top of the optical window 33 to facilitate insertion of the optical film 5 (refer to FIG. 4).

The particle size distribution measuring device 1 of this embodiment uses the reverse Fourier transformation, and glass for comparison (not shown in drawings) is arranged in front of the optical window 33 at a light incoming side.

A discharging port 35 to discharge the sprayed particle group into the outside of the casing 31 is arranged at a rear end portion (opposite side of the introducing port 32) of the inside of the casing body 312.

A connecting member 36 to form a funnel-shaped path is arranged at the discharging port 35, and a discharging mechanism 37 to discharge the sprayed particle group to the outside of the casing 31 is connected at a downstream end of the connecting member 36.

The discharging mechanism 37 is connected to the connecting member 36 and discharges the sprayed particles sprayed into the measuring area P to the outside of the casing 31, and comprises, for example, a discharging pipe. The discharging pipe may comprise multiple components. In addition, the discharging pipe 37 passes an accommodating body 38 arranged on an undersurface of the board 311 and is connected to a vacuum device (not shown in drawings) arranged outside of the casing 31 through a through hole 311a arranged on the board 311. The sprayed particle group is vacuumed up by the vacuum device during the measurement by making use of the discharging mechanism 37. The discharging pipe as being the discharging mechanism 37 may be extended through a rear wall 3123 of the casing body 312 to the outside of the casing 31.

The front panel 313 is fixed to the casing body 312 with a screw, and is provided with the introducing port 32 of a generally circular shape. In this embodiment, the front panel 313 is fixed to the casing body 312 with, for example, four screws in order to make the front panel 313 detachable with ease.

The introducing port 32 introduces the sprayed particle group sprayed from the nozzle into the inside of the casing 31 with the nozzle located close to or inserted into the introducing port 32.

A guiding part 8 to make it easy to locate the nozzle close to or to insert the nozzle into the introducing port 32 is arranged at the outside of the introducing port 32.

In addition, the front panel 313 further comprises an introducing pipe 9 that is arranged continuous to the introducing port 32. The introducing pipe 9 is a cylindrical pipe whose opening is arranged to face the measuring area P. The introducing pipe 9 and the guiding part 8 may be of an integrated body, or may be of separated bodies.

The introducing pipe 9 prevents the sprayed particle group sprayed from the nozzle from spreading and keeps the inside of the casing 31 not to become dirty more than necessary. In addition, the introducing pipe 9 can be dismounted so as to facilitate maintenance of the introducing pipe 9 and to make it possible to exchange the introducing pipe 9 with a different kind (for example, length or diameter) of the introducing pipe 9.

Furthermore, a handle 3131 is arranged at a bottom of the outside of the front panel 313 so as to facilitate handling of the front panel 313. A numerical code 3124 in FIG. 4 through FIG. 6 is a handle that is mounted on a rear wall 3123 and that facilitates mounting or dismounting the spray measuring system 3 on or from the device body 2 in conjunction with the handle 3131 mounted on the front panel 313.

A tray 10 is arranged at the bottom of the casing 31 having the above-mentioned structure, namely on an upper face of the board 311.

The tray 10 is to accommodate liquid generated by liquefying the sprayed particle group, and in a rectangular shape that almost covers the bottom of the inside of the casing 31. In addition, the tray 10 is dismountably arranged on the upper face of the board 311 in order to facilitate maintenance.

In this embodiment, a projecting wall 3123 that projects inward of the side wall 3121 of the casing 31 is arranged, as shown in FIG. 6, especially in FIG. 7, to make almost all of the liquid flow into the tray 10, namely, to prevent the liquid from flowing into a gap formed between the side wall 3121 of the casing 31 and the tray 10. A height where the projecting wall 3123 is arranged is almost the same height which allows the tray 10 to be inserted into a space between the lower face of the board 311 and the projecting wall 3123.

Next, an operation to exchange the ordinary measuring system 4 and the spray measuring system 3 of the particle size distribution measuring device 1 having the above-mentioned structure will be explained.

First, a tube connected to the cell 41 of the ordinary measuring system 4 is dismounted in a state that the ordinary measuring system 4 is mounted on the device body 2. Then the ordinary measuring system 4 is dismounted from the device body 2 by operating the handle 421 arranged on the cell holding member 42 of the ordinary measuring system 4. Next, the spray measuring system 3 is mounted on the inside of the measuring system accommodating space S1 of the device body 2. More concretely, the casing 31 is placed on the rail member 231 arranged in the measuring system accommodating space S1 so as to mount the spray measuring system 3.

In order to measure the sprayed particle group by the use of the particle size distribution measuring device 1 having the above-mentioned structure, a blank measurement is previously conducted prior to an actual measurement. When the sprayed particle group is sprayed from the nozzle, a sensor that monitors the light intensity of inside the device 1 detects that the sprayed particle group is sprayed and measurement is initiated with the detected signal as being a trigger. At this time, the sensor may comprise the light source 21 and the light detector 22.

Effect of this Embodiment

In accordance with the particle size distribution measuring device 1 of this embodiment having the above-mentioned structure, the sprayed particle group sprayed from the nozzle and a conventional ordinary particle group other than the sprayed particle group can be measured with a single particle size distribution measuring device 1. As a result, it is possible to enrich applications of the particle size distribution measuring device 1.

In addition, since the spray measuring system 3 is integrally formed and the spray measuring system 3 can be mounted on the device body 2 just by mounting the casing 31 on the device body 2, it is possible to mount the spray measuring system 3 on the device body 2 with ease.

Furthermore, since the measuring are P is covered by the casing 31, it is possible to measure the sprayed particle group stably without receiving an effect of disturbance such as the wind or the light from the outside and without contaminating the device body 2. In addition, it is possible to conduct the measurement safely even though the sprayed particle group is a measuring sample that is harmful to human body or environment such as solvent, pesticide or insecticide.

In addition, since the optical film 5 is attached to the optical window 33, it is possible to exchange the optical film 5 at low cost in case the optical film 5 becomes dirty.

Furthermore, since the front panel 31 can be dismounted from the casing body 312, it is possible to spray the sprayed particle group at any arbitrary position in case the front panel 313 is dismounted.

In addition, since a distance between the sprayed position and the measuring area P can be adjusted, it is possible to conduct a measurement wherein a relationship between the distance from the sprayed position and the particle is quantitative.

Other Modified Embodiment

The present claimed invention is not limited to the above-mentioned embodiment. In the following explanation, the same numerical code is given to a component corresponding to the above-mentioned embodiment.

Figure 8:
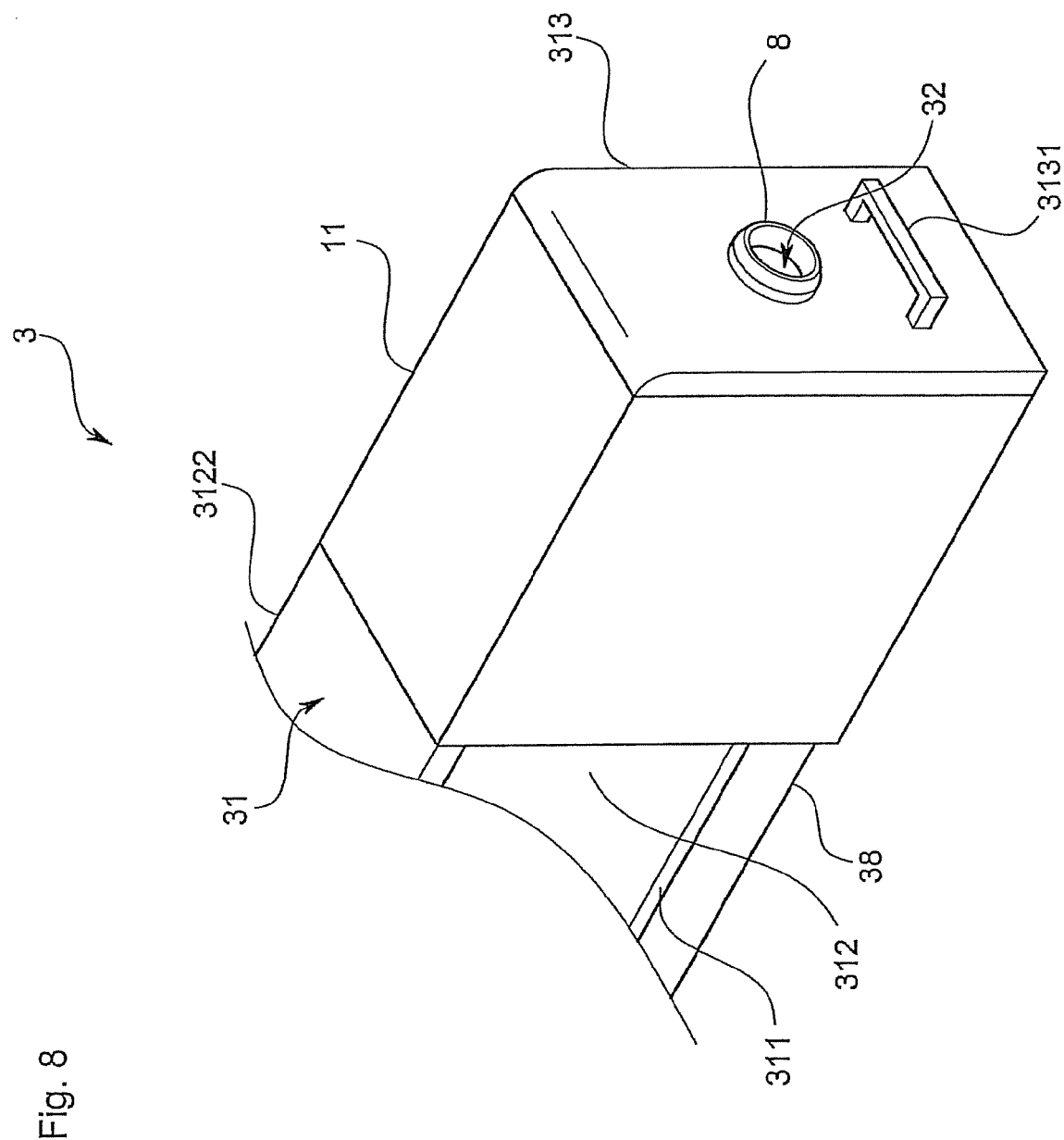
FIG. 8 is a longitudinal sectional view of a spray measuring system in accordance with a modified embodiment.

For example, the front panel 313 can be dismounted from the casing body 312 in the above-mentioned embodiment, however, a distance change tube body 11 to vary a distance between the measuring area P and the introducing port 32 may be arranged between the casing body 312 and the front panel 313, as shown in FIG. 8. The distance change tube body 11 is tubular cuboid whose one end opening is connected to the casing body 312 and whose other end opening is closed by the front panel 313.

In addition, the length of the introducing pipe 9 may be adjustable. More concretely, the introducing pipe 9 may be of, for example, nested structure. With this structure, since it is possible to adjust the sprayed position, the particle size distribution measuring device 1 can be used for various measurements.

Furthermore, a mist catcher may be arranged between the measuring area P and the discharging port 35. This arrangement makes it possible to prevent the sprayed particle group from being vacuumed up into the vacuum device. With this arrangement, it is possible to keep the inside of the vacuum device dry and to lessen the sprayed particle group in the discharged gas discharged from the vacuum device.

In addition, the liquid collected by the mist catcher may flow into the tray 10.

In the above-mentioned embodiment, the reverse Fourier transformation is conducted to measure the particle size distribution, however, Fourier transformation may be conducted to measure the particle size distribution.

In addition, a part or all of the above-mentioned embodiment or the modified embodiment may be appropriately combined, and it is a matter of course that the present claimed invention is not limited to the above-mentioned embodiments and may be variously modified without departing from a spirit of the invention.

The invention claimed is:

1. A particle size distribution measuring device that measures particle size distribution of a particle group, comprising:
    a device body comprising a light source that irradiates light on the particle group and a light detector that detects intensity of diffracted light or scattered light generated by irradiation of the light,
    a spray measuring system that introduces a sprayed particle group as being the particle group sprayed from a nozzle into a measuring area between the light source and the light detector, and
    an ordinary measuring system that arranges a measuring cell that accommodates an ordinary particle group as being a particle group other than the sprayed particle group between the light source and the light detector are arranged to be exchangeable for each other;
    wherein the spray measuring system comprises:
        a casing that is mounted on the device body and inside of which a measuring area to measure the sprayed particle group is provided;

an introducing port that is arranged on the casing and that introduces the sprayed particle group into inside of the casing; and an optical window that is arranged on the casing and between the measuring area and the light source, and between the measuring area and the light detector, and the spray measuring system is mounted on the device body by mounting the casing on the device body in a state that the ordinary measuring system is dismounted from the device body.

2. The particle size distribution measuring device described in claim 1, and further comprising an introducing pipe that is arranged continuously to the introducing port and that opens toward the measuring area.

3. The particle size distribution measuring device described in claim 1, wherein a distance between the measuring area and the introducing port is arranged to be variable.

4. The particle size distribution measuring device described in claim 3, wherein the casing comprises a casing body that has the optical window and that covers the measuring area and a front panel that has the introducing port, and further comprising a distance change tube body that is arranged between the front panel and the casing body and that changes the distance between the measuring area and the introducing port.

5. The particle size distribution measuring device described in claim 1, and further comprising:

a discharging port that is arranged in the casing and that discharges the sprayed particle group to the outside and a vacuum mechanism that vacuums up the sprayed particle group from the discharging port.

6. The particle size distribution measuring device described in claim 1, and further comprising a tray that is arranged on an under surface of the casing and that accommodates liquid generated at a time when the sprayed particle group is liquefied.

7. The particle size distribution measuring device described in claim 1, wherein a disposable optical film is arranged on the optical window.

* * * * *